(12) United States Patent
Bouwstra et al.

(10) Patent No.: US 8,101,205 B2
(45) Date of Patent: *Jan. 24, 2012

(54) CONTROLLED RELEASE COMPOSITION

(75) Inventors: Jan Bastiaan Bouwstra, Tilburg (NL); Marc Sutter, Tilburg (NL); Sebastianus Gerardus Kluijtmans, Tilburg (NL); Wilhelmus Everhardus Hennink, Tilburg (NL); Wim Jiskoot, Tilburg (NL)

(73) Assignee: Fujifilm Manufacturing Europe B.V., Tilburg (NL)

( * ) Notice: Subject to any disclaimer, the term of this patent is extended or adjusted under 35 U.S.C. 154(b) by 13 days.

This patent is subject to a terminal disclaimer.

(21) Appl. No.: 12/528,071

(22) PCT Filed: Feb. 21, 2008

(86) PCT No.: PCT/NL2008/050106
§ 371 (c)(1),
(2), (4) Date: Sep. 30, 2009

(87) PCT Pub. No.: WO2008/103046
PCT Pub. Date: Aug. 28, 2008

(65) Prior Publication Data
US 2010/0048481 A1 Feb. 25, 2010

(30) Foreign Application Priority Data
Feb. 21, 2007 (EP) .................................. 07102838

(51) Int. Cl.
*A61K 9/26* (2006.01)
(52) U.S. Cl. .......................................................... 424/469
(58) Field of Classification Search .................... 424/469
See application file for complete search history.

(56) References Cited

U.S. PATENT DOCUMENTS

| | | | |
|---|---|---|---|
| 4,855,134 A | 8/1989 | Yamahira et al. | 424/85.7 |
| 5,002,769 A | 3/1991 | Friedman | 424/422 |
| 5,023,082 A | 6/1991 | Friedman et al. | 424/426 |
| 5,399,361 A | 3/1995 | Song et al. | 424/486 |
| 5,512,301 A | 4/1996 | Song et al. | 424/484 |
| 5,597,578 A | 1/1997 | Brown et al. | 424/422 |
| 5,733,994 A | 3/1998 | Koepff et al. | 527/207 |
| 5,897,879 A | 4/1999 | Friedman et al. | 424/486 |
| 6,068,854 A | 5/2000 | Wunderlich et al. | 424/464 |
| 6,140,072 A | 10/2000 | Ferrari et al. | 435/69.1 |
| 6,150,081 A | 11/2000 | Van Heerde et al. | 430/569 |
| 6,342,250 B1 | 1/2002 | Masters | 424/484 |
| 6,458,386 B1 | 10/2002 | Schacht et al. | 424/488 |
| 6,831,058 B1 | 12/2004 | Ikada et al. | 514/2 |
| 6,992,172 B1 | 1/2006 | Chang et al. | 530/354 |
| 7,517,954 B2 | 4/2009 | Bouwstra et al. | 530/350 |
| 2002/0028243 A1 | 3/2002 | Masters | 424/484 |
| 2002/0106410 A1 | 8/2002 | Masters | 424/484 |
| 2003/0007991 A1 | 1/2003 | Masters | 424/423 |
| 2003/0064074 A1 | 4/2003 | Chang et al. | 424/184.1 |
| 2004/0237663 A1 | 12/2004 | Farber et al. | 73/861.08 |
| 2005/0058703 A1 | 3/2005 | Chang et al. | 424/456 |
| 2005/0119170 A1 | 6/2005 | Bouwstra et al. | 514/12 |
| 2005/0147690 A1 | 7/2005 | Masters et al. | 424/499 |
| 2005/0208141 A1 | 9/2005 | Farber et al. | 424/488 |
| 2005/0229264 A1 | 10/2005 | Chang et al. | 800/8 |
| 2005/0238663 A1 | 10/2005 | Hunt | 424/239.1 |
| 2006/0024346 A1 | 2/2006 | Brody et al. | 424/423 |
| 2006/0024361 A1 | 2/2006 | Odidi et al. | 424/464 |
| 2006/0068013 A1 | 3/2006 | DiTizio et al. | 424/484 |
| 2006/0121609 A1 | 6/2006 | Yannas et al. | 435/395 |
| 2006/0147501 A1 | 7/2006 | Hillas et al. | 424/443 |
| 2006/0177492 A1 | 8/2006 | Yunoki et al. | 424/445 |
| 2006/0204511 A1 | 9/2006 | Bouwstra et al. | 424/185.1 |
| 2006/0241032 A1 | 10/2006 | Bouwstra et al. | 514/12 |
| 2006/0251719 A1 | 11/2006 | Tabata | 424/468 |
| 2007/0004034 A1 | 1/2007 | Bouwstra et al. | 435/289.1 |
| 2007/0009580 A1 | 1/2007 | DiCosmo et al. | 424/443 |
| 2007/0031501 A1 | 2/2007 | Van Es et al. | 424/488 |
| 2007/0190153 A1 | 8/2007 | Farber | 424/488 |
| 2007/0196496 A1 | 8/2007 | Farber et al. | 424/488 |
| 2008/0107666 A1 | 5/2008 | van Es et al. | 424/185.1 |
| 2008/0113910 A1 | 5/2008 | Bouwstra et al. | 514/12 |
| 2008/0114078 A1 | 5/2008 | Bouwstra et al. | 514/774 |
| 2008/0167446 A1 | 7/2008 | Bouwstra et al. | 530/354 |
| 2008/0274957 A1 | 11/2008 | Bouwstra et al. | 514/12 |
| 2009/0143568 A1 | 6/2009 | Chang et al. | 530/354 |

FOREIGN PATENT DOCUMENTS

| | | |
|---|---|---|
| EP | 1 607 085 | 12/2005 |
| JP | 2005-211477 | 8/2005 |
| WO | WO 98/55161 | 12/1998 |
| WO | WO 2004/056976 | 7/2004 |
| WO | WO 2004/085473 | 10/2004 |
| WO | WO 2005/011739 | 2/2005 |
| WO | WO 2007/073190 | 6/2007 |

OTHER PUBLICATIONS

Werten et al., "High-yield Secretion of Recombinant Gelatins by *Pichia pastoris*", Yeast, 15:1087-1096 (1999).
Báez et al., "Recombinant microbial systems for the production of human collagen and gelatin", Appl. Microbiol Biotechnol., 69:245-252 (2005).
Werten et al., "Secreted production of a custom-designed, highly hydrophilic gelatin in *Pichia pastoris*", Protein Engineering, 14(6):447-454 (2001).
Olsen et al., "Recombinant collagen and gelatin for drug delivery", Advanced Drug Delivery Reviews, Amsterdam, NL, 55(12):1547-1567 (2003).
Sutter et al., "Recombinant gelatin hydrogels for the sustained release of proteins", Journal of Controlled Release, 119:301-312 (2007).
Extracts from gmap-gelatin.com, dated Aug. 25, 2006.

*Primary Examiner* — Maryam Monshipouri
(74) *Attorney, Agent, or Firm* — Morgan, Lewis & Bockius LLP

(57) ABSTRACT

The invention relates to the field of pharmacology. More specific, the invention relates to a controlled release composition.
This invention is related to a controlled release composition comprising a cross-linked gelatin and at least one therapeutic protein wherein the ratio of the average mesh size ($\xi$) of the gelatin matrix and the average hydrodynamic radius ($R_H$) of the therapeutic protein is smaller than 2, preferably smaller than 1.5.

20 Claims, 4 Drawing Sheets

```
  1 GAPGAPGLQGAPGLQGMPGERGAAGLPGPK
 31 GERGDAGPKGADGAPGAPGLQGMPGERGAA
 61 GLPGPKGERGDAGPKGADGAPGKDGVRGLA
 91 GPIGPPGERGAAGLPGPKGERGDAGPKGAD
121 GAPGKDGVRGLAGPIGPPGPAGAPGAPGLQ
151 GMPGERGAAGLPGPKGERGDAGPKGADGAP
181 GKDGVRGLAGPI
```

Fig. 3

```
  1 GAPGAPGLQGAPGLQGMPGERGAAGLPGPK
 31 GERGDAGPKGADGAPGAPGLQGMPGERGAA
 61 GLPGPKGERGDAGPKGADGAPGKDGVRGLA
 91 GPIGPPGERGAAGLPGPKGERGDAGPKGAD
121 GAPGKDGVRGLAGPIGPPGPAGAPGAPGLQ
151 GMPGERGAAGLPGPKGERGDAGPKGADGAP
181 GKDGVRGLAGPPGAPGLQGAPGLQGMPGER
211 GAAGLPGPKGERGDAGPKGADGAPGAPGLQ
241 GMPGERGAAGLPGPKGERGDAGPKGADGAP
271 GKDGVRGLAGPIGPPGERGAAGLPGPKGER
301 GDAGPKGADGAPGKDGVRGLAGPIGPPGPA
331 GAPGAPGLQGMPGERGAAGLPGPKGERGDA
361 GPKGADGAPGKDGVRGLAGPPGAPGLQGAP
391 GLQGMPGERGAAGLPGPKGERGDAGPKGAD
421 GAPGAPGLQGMPGERGAAGLPGPKGERGDA
451 GPKGADGAPGKDGVRGLAGPIGPPGERGAA
481 GLPGPKGERGDAGPKGADGAPGKDGVRGLA
511 GPIGPPGPAGAPGAPGLQGMPGERGAAGLP
541 GPKGERGDAGPKGADGAPGKDGVRGLAGPP
571 GAPGLQGAPGLQGMPGERGAAGLPGPKGER
601 GDAGPKGADGAPGAPGLQGMPGERGAAGLP
631 GPKGERGDAGPKGADGAPGKDGVRGLAGPI
661 GPPGERGAAGLPGPKGERGDAGPKGADGAP
691 GKDGVRGLAGPIGPPGPAGAPGAPGLQGMP
721 GERGAAGLPGPKGERGDAGPKGADGAPGKD
751 GVRGLAGPPGAPGLQGAPGLQGMPGERGAA
781 GLPGPKGERGDAGPKGADGAPGAPGLQGMP
811 GERGAAGLPGPKGERGDAGPKGADGAPGKD
841 GVRGLAGPIGPPGERGAAGLPGPKGERGDA
871 GPKGADGAPGKDGVRGLAGPIGPPGPAGAP
901 GAPGLQGMPGERGAAGLPGPKGERGDAGPK
931 GADGAPGKDGVRGLAGPPG
```

Fig. 4

```
  1 GPPGEPGNPGSPGNQGQPGNKGSPGNPGQP
 31 GNEGQPGQPGQNGQPGEPGSNGPQGSQGNP
 61 GKNGQPGSPGSQGSPGNQGSPGQPGNPGQP
 91 GEQGKPGNQGPAGEPGNPGSPGNQGQPGNK
121 GSPGNPGQPGNEGQPGQPGQNGQPGEPGSN
151 GPQGSQGNPGKNGQPGSPGSQGSPGNQGSP
181 GQPGNPGQPGEQGKPGNQGPAGEPGNPGSP
211 GNQGQPGNKGSPGNPGQPGNEGQPGQPGQN
241 GQPGEPGSNGPQGSQGNPGKNGQPGSPGSQ
271 GSPGNQGSPGQPGNPGQPGEQGKPGNQGPA
301 GEPGNPGSPGNQGQPGNKGSPGNPGQPGNE
331 GQPGQPGQNGQPGEPGSNGPQGSQGNPGKN
361 GQPGSPGSQGSPGNQGSPGQPGNPGQPGEQ
391 GKPGNQGPAGG
```

SEQUENCE LISTING

<160> NUMBER OF SEQ ID NOS: 4

<210> SEQ ID NO 1
<211> LENGTH: 821
<212> TYPE: PRT
<213> ORGANISM: Artificial sequence
<220> FEATURE:
<223> OTHER INFORMATION: HU4 gelatin

<400> SEQUENCE: 1

```
Gly Pro Pro Gly Glu Pro Gly Pro Thr Gly Leu Pro Gly Pro Pro Gly
1               5                   10                  15

Glu Arg Gly Gly Pro Gly Ser Arg Gly Phe Pro Gly Ala Asp Gly Val
            20                  25                  30

Ala Gly Pro Lys Gly Pro Ala Gly Glu Arg Gly Ser Pro Gly Pro Ala
        35                  40                  45

Gly Pro Lys Gly Ser Pro Gly Glu Ala Gly Arg Pro Gly Glu Ala Gly
    50                  55                  60

Leu Pro Gly Ala Lys Gly Leu Thr Gly Ser Pro Gly Ser Pro Gly Pro
65                  70                  75                  80

Asp Gly Lys Thr Gly Pro Pro Gly Pro Ala Gly Gln Asp Gly Arg Pro
                85                  90                  95

Gly Pro Pro Gly Pro Pro Gly Ala Arg Gly Gln Ala Gly Val Met Gly
            100                 105                 110

Phe Pro Gly Pro Lys Gly Ala Ala Gly Glu Pro Gly Lys Ala Gly Glu
        115                 120                 125

Arg Gly Val Pro Gly Pro Pro Gly Ala Val Gly Pro Ala Gly Lys Asp
    130                 135                 140

Gly Glu Ala Gly Ala Gln Gly Pro Pro Gly Pro Ala Gly Pro Ala Gly
145                 150                 155                 160

Glu Arg Gly Glu Gln Gly Pro Ala Gly Ser Pro Gly Phe Gln Gly Leu
                165                 170                 175

Pro Gly Pro Ala Gly Pro Pro Gly Glu Ala Gly Lys Pro Gly Glu Gln
            180                 185                 190

Gly Val Pro Gly Asp Leu Gly Ala Pro Gly Pro Ser Gly Pro Ala Gly
        195                 200                 205

Glu Pro Gly Pro Thr Gly Leu Pro Gly Pro Pro Gly Glu Arg Gly Gly
    210                 215                 220

Pro Gly Ser Arg Gly Phe Pro Gly Ala Asp Gly Val Ala Gly Pro Lys
225                 230                 235                 240

Gly Pro Ala Gly Glu Arg Gly Ser Pro Gly Pro Ala Gly Pro Lys Gly
                245                 250                 255

Ser Pro Gly Glu Ala Gly Arg Pro Gly Glu Ala Gly Leu Pro Gly Ala
            260                 265                 270

Lys Gly Leu Thr Gly Ser Pro Gly Ser Pro Gly Pro Asp Gly Lys Thr
        275                 280                 285

Gly Pro Pro Gly Pro Ala Gly Gln Asp Gly Arg Pro Gly Pro Pro Gly
    290                 295                 300

Pro Pro Gly Ala Arg Gly Gln Ala Gly Val Met Gly Phe Pro Gly Pro
305                 310                 315                 320

Lys Gly Ala Ala Gly Glu Pro Gly Lys Ala Gly Glu Arg Gly Val Pro
                325                 330                 335

Gly Pro Pro Gly Ala Val Gly Pro Ala Gly Lys Asp Gly Glu Ala Gly
            340                 345                 350
```

-continued

```
Ala Gln Gly Pro Pro Gly Pro Ala Gly Pro Ala Gly Glu Arg Gly Glu
        355                 360                 365

Gln Gly Pro Ala Gly Ser Pro Gly Phe Gln Gly Leu Pro Gly Pro Ala
    370                 375                 380

Gly Pro Pro Gly Glu Ala Gly Lys Pro Gly Glu Gln Gly Val Pro Gly
385                 390                 395                 400

Asp Leu Gly Ala Pro Gly Pro Ser Gly Ala Gly Glu Pro Gly Pro
                405                 410                 415

Thr Gly Leu Pro Gly Pro Pro Gly Glu Arg Gly Pro Gly Ser Arg
                420                 425                 430

Gly Phe Pro Gly Ala Asp Gly Val Ala Gly Pro Lys Gly Pro Ala Gly
        435                 440                 445

Glu Arg Gly Ser Pro Gly Pro Ala Gly Pro Lys Gly Ser Pro Gly Glu
    450                 455                 460

Ala Gly Arg Pro Gly Glu Ala Gly Leu Pro Gly Ala Lys Gly Leu Thr
465                 470                 475                 480

Gly Ser Pro Gly Ser Pro Gly Pro Asp Gly Lys Thr Gly Pro Pro Gly
                485                 490                 495

Pro Ala Gly Gln Asp Gly Arg Pro Gly Pro Pro Gly Pro Pro Gly Ala
            500                 505                 510

Arg Gly Gln Ala Gly Val Met Gly Phe Pro Gly Pro Lys Gly Ala Ala
        515                 520                 525

Gly Glu Pro Gly Lys Ala Gly Glu Arg Gly Val Pro Gly Pro Pro Gly
    530                 535                 540

Ala Val Gly Pro Ala Gly Lys Asp Gly Glu Ala Gly Ala Gln Gly Pro
545                 550                 555                 560

Pro Gly Pro Ala Gly Pro Ala Gly Glu Arg Gly Glu Gln Gly Pro Ala
                565                 570                 575

Gly Ser Pro Gly Phe Gln Gly Leu Pro Gly Pro Ala Gly Pro Pro Gly
            580                 585                 590

Glu Ala Gly Lys Pro Gly Glu Gln Gly Val Pro Gly Asp Leu Gly Ala
        595                 600                 605

Pro Gly Pro Ser Gly Pro Ala Gly Glu Pro Gly Pro Thr Gly Leu Pro
    610                 615                 620

Gly Pro Pro Gly Glu Arg Gly Pro Gly Ser Arg Gly Phe Pro Gly
625                 630                 635                 640

Ala Asp Gly Val Ala Gly Pro Lys Gly Pro Ala Gly Glu Arg Gly Ser
                645                 650                 655

Pro Gly Pro Ala Gly Pro Lys Gly Ser Pro Gly Glu Ala Gly Arg Pro
            660                 665                 670

Gly Glu Ala Gly Leu Pro Gly Ala Lys Gly Leu Thr Gly Ser Pro Gly
        675                 680                 685

Ser Pro Gly Pro Asp Gly Lys Thr Gly Pro Pro Gly Pro Ala Gly Gln
    690                 695                 700

Asp Gly Arg Pro Gly Pro Pro Gly Pro Pro Gly Ala Arg Gly Gln Ala
705                 710                 715                 720

Gly Val Met Gly Phe Pro Gly Pro Lys Gly Ala Ala Gly Glu Pro Gly
                725                 730                 735

Lys Ala Gly Glu Arg Gly Val Pro Gly Pro Pro Gly Ala Val Gly Pro
            740                 745                 750

Ala Gly Lys Asp Gly Glu Ala Gly Ala Gln Gly Pro Pro Gly Pro Ala
        755                 760                 765

Gly Pro Ala Gly Glu Arg Gly Glu Gln Gly Pro Ala Gly Ser Pro Gly
    770                 775                 780
```

```
Phe Gln Gly Leu Pro Gly Pro Ala Gly Pro Gly Glu Ala Gly Lys
785                 790                 795                 800

Pro Gly Glu Gln Gly Val Pro Gly Asp Leu Gly Ala Pro Pro Ser
            805                 810                 815

Gly Pro Ala Gly Gly
            820

<210> SEQ ID NO 2
<211> LENGTH: 192
<212> TYPE: PRT
<213> ORGANISM: Artificial sequence
<220> FEATURE:
<223> OTHER INFORMATION: CBE

<400> SEQUENCE: 2

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Ile
            180                 185                 190

<210> SEQ ID NO 3
<211> LENGTH: 949
<212> TYPE: PRT
<213> ORGANISM: Artificial sequence
<220> FEATURE:
<223> OTHER INFORMATION: CBE5

<400> SEQUENCE: 3

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80
```

-continued

```
Pro Gly Lys Asp Gly Val Arg Gly Leu Ala Gly Pro Ile Pro Pro
             85                  90                  95
Gly Glu Arg Gly Ala Ala Gly Leu Pro Gly Pro Lys Gly Glu Arg Gly
            100                 105                 110
Asp Ala Gly Pro Lys Gly Ala Asp Gly Ala Pro Gly Lys Asp Gly Val
            115                 120                 125
Arg Gly Leu Ala Gly Pro Ile Gly Pro Pro Gly Ala Gly Ala Pro
130                 135                 140
Gly Ala Pro Gly Leu Gln Gly Met Pro Gly Glu Arg Gly Ala Ala Gly
145                 150                 155                 160
Leu Pro Gly Pro Lys Gly Glu Arg Gly Asp Ala Gly Pro Lys Gly Ala
                165                 170                 175
Asp Gly Ala Pro Gly Lys Asp Gly Val Arg Gly Leu Ala Gly Pro Pro
            180                 185                 190
Gly Ala Pro Gly Leu Gln Gly Ala Pro Gly Leu Gln Gly Met Pro Gly
            195                 200                 205
Glu Arg Gly Ala Ala Gly Leu Pro Gly Pro Lys Gly Glu Arg Gly Asp
210                 215                 220
Ala Gly Pro Lys Gly Ala Asp Gly Ala Pro Gly Ala Pro Gly Leu Gln
225                 230                 235                 240
Gly Met Pro Gly Glu Arg Gly Ala Ala Gly Leu Pro Gly Pro Lys Gly
                245                 250                 255
Glu Arg Gly Asp Ala Gly Pro Lys Gly Ala Asp Gly Ala Pro Gly Lys
                260                 265                 270
Asp Gly Val Arg Gly Leu Ala Gly Pro Ile Gly Pro Pro Gly Glu Arg
            275                 280                 285
Gly Ala Ala Gly Leu Pro Gly Pro Lys Gly Glu Arg Gly Asp Ala Gly
            290                 295                 300
Pro Lys Gly Ala Asp Gly Ala Pro Gly Lys Asp Gly Val Arg Gly Leu
305                 310                 315                 320
Ala Gly Pro Ile Gly Pro Pro Gly Pro Ala Gly Ala Pro Gly Ala Pro
                325                 330                 335
Gly Leu Gln Gly Met Pro Gly Glu Arg Gly Ala Ala Gly Leu Pro Gly
                340                 345                 350
Pro Lys Gly Glu Arg Gly Asp Ala Gly Pro Lys Gly Ala Asp Gly Ala
            355                 360                 365
Pro Gly Lys Asp Gly Val Arg Gly Leu Ala Gly Pro Pro Gly Ala Pro
            370                 375                 380
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
                405                 410                 415
Lys Gly Ala Asp Gly Ala Pro Gly Ala Pro Gly Leu Gln Gly Met Pro
            420                 425                 430
Gly Glu Arg Gly Ala Ala Gly Leu Pro Gly Pro Lys Gly Glu Arg Gly
            435                 440                 445
Asp Ala Gly Pro Lys Gly Ala Asp Gly Ala Pro Gly Lys Asp Gly Val
            450                 455                 460
Arg Gly Leu Ala Gly Pro Ile Gly Pro Pro Gly Glu Arg Gly Ala Ala
465                 470                 475                 480
Gly Leu Pro Gly Pro Lys Gly Glu Arg Gly Asp Ala Gly Pro Lys Gly
                485                 490                 495
Ala Asp Gly Ala Pro Gly Lys Asp Gly Val Arg Gly Leu Ala Gly Pro
```

```
                500             505             510
Ile Gly Pro Pro Gly Pro Ala Gly Ala Pro Gly Leu Gln
            515             520             525
Gly Met Pro Gly Glu Arg Gly Ala Ala Gly Leu Pro Gly Pro Lys Gly
            530             535             540
Glu Arg Gly Asp Ala Gly Pro Lys Gly Ala Asp Gly Ala Pro Gly Lys
545             550             555             560
Asp Gly Val Arg Gly Leu Ala Gly Pro Pro Gly Ala Pro Gly Leu Gln
                565             570             575
Gly Ala Pro Gly Leu Gln Gly Met Pro Gly Glu Arg Gly Ala Ala Gly
            580             585             590
Leu Pro Gly Pro Lys Gly Glu Arg Gly Asp Ala Gly Pro Lys Gly Ala
            595             600             605
Asp Gly Ala Pro Gly Ala Pro Gly Leu Gln Gly Met Pro Gly Glu Arg
            610             615             620
Gly Ala Ala Gly Leu Pro Gly Pro Lys Gly Glu Arg Gly Asp Ala Gly
625             630             635             640
Pro Lys Gly Ala Asp Gly Ala Pro Gly Lys Asp Gly Val Arg Gly Leu
                645             650             655
Ala Gly Pro Ile Gly Pro Pro Gly Glu Arg Gly Ala Ala Gly Leu Pro
            660             665             670
Gly Pro Lys Gly Glu Arg Gly Asp Ala Gly Pro Lys Gly Ala Asp Gly
            675             680             685
Ala Pro Gly Lys Asp Gly Val Arg Gly Leu Ala Gly Pro Ile Gly Pro
            690             695             700
Pro Gly Pro Ala Gly Ala Pro Gly Ala Pro Gly Leu Gln Gly Met Pro
705             710             715             720
Gly Glu Arg Gly Ala Ala Gly Leu Pro Gly Pro Lys Gly Glu Arg Gly
                725             730             735
Asp Ala Gly Pro Lys Gly Ala Asp Gly Ala Pro Gly Lys Asp Gly Val
            740             745             750
Arg Gly Leu Ala Gly Pro Pro Gly Ala Pro Gly Leu Gln Gly Ala Pro
            755             760             765
Gly Leu Gln Gly Met Pro Gly Glu Arg Gly Ala Ala Gly Leu Pro Gly
            770             775             780
Pro Lys Gly Glu Arg Gly Asp Ala Gly Pro Lys Gly Ala Asp Gly Ala
785             790             795             800
Pro Gly Ala Pro Gly Leu Gln Gly Met Pro Gly Glu Arg Gly Ala Ala
                805             810             815
Gly Leu Pro Gly Pro Lys Gly Glu Arg Gly Asp Ala Gly Pro Lys Gly
            820             825             830
Ala Asp Gly Ala Pro Gly Lys Asp Gly Val Arg Gly Leu Ala Gly Pro
            835             840             845
Ile Gly Pro Pro Gly Glu Arg Gly Ala Ala Gly Leu Pro Gly Pro Lys
            850             855             860
Gly Glu Arg Gly Asp Ala Gly Pro Lys Gly Ala Asp Gly Ala Pro Gly
865             870             875             880
Lys Asp Gly Val Arg Gly Leu Ala Gly Pro Ile Gly Pro Pro Gly Pro
                885             890             895
Ala Gly Ala Pro Gly Ala Pro Gly Leu Gln Gly Met Pro Gly Glu Arg
            900             905             910
Gly Ala Ala Gly Leu Pro Gly Pro Lys Gly Glu Arg Gly Asp Ala Gly
            915             920             925
```

```
Pro Lys Gly Ala Asp Gly Ala Pro Gly Lys Asp Gly Val Arg Gly Leu
        930                 935                 940
Ala Gly Pro Pro Gly
945

<210> SEQ ID NO 4
<211> LENGTH: 401
<212> TYPE: PRT
<213> ORGANISM: Artificial sequence
<220> FEATURE:
<223> OTHER INFORMATION: P4

<400> SEQUENCE: 4

Gly Pro Pro Gly Glu Pro Gly Asn Pro Gly Ser Pro Gly Asn Gln Gly
1               5                   10                  15

Gln Pro Gly Asn Lys Gly Ser Pro Gly Asn Pro Gly Gln Pro Gly Asn
            20                  25                  30

Glu Gly Gln Pro Gly Gln Pro Gly Gln Asn Gly Gln Pro Gly Glu Pro
        35                  40                  45

Gly Ser Asn Gly Pro Gln Gly Ser Gln Gly Asn Pro Gly Lys Asn Gly
    50                  55                  60

Gln Pro Gly Ser Pro Gly Ser Gln Gly Ser Pro Gly Asn Gln Gly Ser
65                  70                  75                  80

Pro Gly Gln Pro Gly Asn Pro Gly Gln Pro Gly Glu Gln Gly Lys Pro
                85                  90                  95

Gly Asn Gln Gly Pro Ala Gly Glu Pro Gly Asn Pro Gly Ser Pro Gly
            100                 105                 110

Asn Gln Gly Gln Pro Gly Asn Lys Gly Ser Pro Gly Asn Pro Gly Gln
        115                 120                 125

Pro Gly Asn Glu Gly Gln Pro Gly Gln Pro Gly Gln Asn Gly Gln Pro
    130                 135                 140

Gly Glu Pro Gly Ser Asn Gly Pro Gln Gly Ser Gln Gly Asn Pro Gly
145                 150                 155                 160

Lys Asn Gly Gln Pro Gly Ser Pro Gly Ser Gln Gly Ser Pro Gly Asn
                165                 170                 175

Gln Gly Ser Pro Gly Gln Pro Gly Asn Pro Gly Gln Pro Gly Glu Gln
            180                 185                 190

Gly Lys Pro Gly Asn Gln Gly Pro Ala Gly Glu Pro Gly Asn Pro Gly
        195                 200                 205

Ser Pro Gly Asn Gln Gly Gln Pro Gly Asn Lys Gly Ser Pro Gly Asn
    210                 215                 220

Pro Gly Gln Pro Gly Asn Glu Gly Gln Pro Gly Gln Pro Gly Gln Asn
225                 230                 235                 240

Gly Gln Pro Gly Glu Pro Gly Ser Asn Gly Pro Gln Gly Ser Gln Gly
                245                 250                 255

Asn Pro Gly Lys Asn Gly Gln Pro Gly Ser Pro Gly Ser Gln Gly Ser
            260                 265                 270

Pro Gly Asn Gln Gly Ser Pro Gly Gln Pro Gly Asn Pro Gly Gln Pro
        275                 280                 285

Gly Glu Gln Gly Lys Pro Gly Asn Gln Gly Pro Ala Gly Glu Pro Gly
    290                 295                 300

Asn Pro Gly Ser Pro Gly Asn Gln Gly Gln Pro Gly Asn Lys Gly Ser
305                 310                 315                 320

Pro Gly Asn Pro Gly Gln Pro Gly Asn Glu Gly Gln Pro Gly Gln Pro
                325                 330                 335

Gly Gln Asn Gly Gln Pro Gly Glu Pro Gly Ser Asn Gly Pro Gln Gly
```

```
                    340                 345                 350
Ser Gln Gly Asn Pro Gly Lys Asn Gly Gln Pro Gly Ser Pro Gly Ser
            355                 360                 365

Gln Gly Ser Pro Gly Asn Gln Gly Ser Pro Gly Gln Pro Gly Asn Pro
        370                 375                 380

Gly Gln Pro Gly Glu Gln Gly Lys Pro Gly Asn Gln Gly Pro Ala Gly
385                 390                 395                 400

Gly
```

US 8,101,205 B2

CONTROLLED RELEASE COMPOSITION

This is a 371 filing based on PCT/NL2008/050106 filed Feb. 21, 2008 and claiming priority from European Application No. 07102838.5, filed Feb. 21, 2007.

FIELD OF INVENTION

The invention relates to the field of pharmacology. More specific, the invention relates to a controlled release composition, a pharmaceutical composition comprising the controlled release composition, a pharmaceutical article comprising the controlled release composition, and to a method for preparing the controlled release composition as well as to the use of a recombinant gelatin for producing the controlled release composition.

PRIOR ART

Maintaining pharmacologically active concentrations of parenterally administered therapeutic proteins over a prolonged period of time can be achieved by structural alteration of the proteins to increase their circulation time and by the use of controlled release formulations. For some proteins, e.g. tissue plasminogen activator, erythropeotin, and interferon, alteration of the protein native structure was a successful approach. In many situations however, the development of a slow release formulation is the more feasible approach. At present, slow release formulations are frequently prepared by encapsulating the protein in a polymeric matrix, from which it is released within several days, weeks, or months, either by diffusion or degradation of the matrix. The preservation of native structure and functionality of the encapsulated protein is a major issue in the development of slow release formulations. Furthermore, the formulations should be well tolerated and with regard to parenteral administration, it is often preferable that they be entirely biodegradable to avoid surgical removal of empty matrices.

Hydrogels are specific types of matrix systems that are attractive for the controlled release of therapeutic proteins. They are formed by physical or chemical cross-linking of hydrophilic polymers, and contain large amounts of water. It is possible to develop hydrogels as implantable or injectable, in-situ gelling systems. The hydrophilicity of hydrogels has been shown to be favorable for preserving the native structure and functionality of the incorporated protein. The high water content and soft consistency of hydrogels minimizes mechanical irritation upon administration. Furthermore, it has been shown that hydrogels are well tolerated and biocompatible in-vivo. Depending on the type of polymer and the type of cross-link, they are also biodegradable.

Polymers for the preparation of hydrogels are commonly classified as natural derived or synthetic. Natural derived polymers like dextrans and gelatins have been used for the development of hydrogels for protein delivery, because these polymers are biocompatible and biodegradable. However, adaptation of natural derived polymers to specific requirements is limited to the chemical derivatization of functional groups in the polymer backbone. In contrast, the backbone of synthetic polymers can be freely defined, which renders greater control of the physicochemical and biological properties of these molecules.

One of the main problems of currently used gelatin based controlled release compositions is that the release of enclosed pharmaceutical is typically preceded by a burst release of said pharmaceutical.

The goal of the present invention is to at least partly decrease, but preferably completely abolish, said initial burst of enclosed pharmaceutical.

SUMMARY OF THE INVENTION

The present invention provide a solution for the initial burst of an enclosed pharmaceutical in a controlled release composition, by providing a controlled release composition comprising a cross-linked gelatin and at least one therapeutic protein wherein the ratio of the average mesh size ($\xi$) of the gelatin matrix and the average hydrodynamic radius ($R_H$) of said therapeutic protein is smaller than 2, preferably smaller than 1.5.

The cross-linking process by which the crosslinked gelatine is prepared is essentially chemical. The term chemical crosslinking as used herein refers to the fact that the crosslinking is achieved by the addition of cross-linking agents or the modification of the gelatin with cross-linkable groups. It must be expressly noted that the term crosslinking as used herein does not refer to the crosslinking between lysine residues in hydroxylated gelatin. In natural collagens (e.g. from bone or hide) from which natural gelatins are derived a certain amount of the proline and lysine residues are hydroxylated by hydroxylases. The resulting hydroxylated lysyl residues present within and between individual collagen molecules can be biosynthetically crosslinked in vivo thereby crosslinking the collagens into fibrillar structures. While the derived natural gelatin lost the fibrillar structure of collagen, parts of the biosynthetic crosslinks will remain. This type of crosslinking is not desirable, as it cannot be controlled. Moreover, this type of crosslinking is inherently present in natural gelatins, that is, from the moment of its production, and to varying degrees. In the present invention, the crosslinking should only occur when the gelatin is mixed with the pharmaceutical active. Hence, it is desirable that the commencement of crosslinking can be controlled, as well as the level thereof. Hence, a gelatin used in aspects of the present invention preferably is a recombinant gelatin more preferably produced in a expression system that lacks the biosynthetic enzymes for hydroxylation and biosynthetic crosslinking of lysine residues and therefore comprises essentially no hydroxylysine crosslinks (is essentially free of hydroxylysine crosslinks). Also the gelatin used in aspects of the present invention is essentially free of hydroxyproline residues.

The invention is furthermore directed to a pharmaceutical composition and a pharmaceutical article using the inventive controlled release composition. The invention is furthermore directed to a method for the preparation of the inventive controlled release compositions and to a method of treating a subject with an effective amount of the inventive controlled release composition.

DETAILED DESCRIPTION

In a first embodiment, the invention provides a controlled release composition comprising a cross-linked gelatin and at least one therapeutic protein wherein the ratio of the average mesh size ($\xi$) of the gelatin matrix and the average hydrodynamic radius ($R_H$) of said therapeutic protein is smaller than 2, preferably smaller than 1.5.

A controlled release composition (or system) or a hydrogel (the terms are used interchangeably herein) typically refers to a three-dimensional network of polymer chains comprising a substantial amount of water. Depending on the application, i.e. desired release profile of the included pharmaceutical and mechanical stress to which the hydrogel is subjected, several types of hydrogels can be used. For example hydrogels that are very stiff and inelastic containing 40%-60% of water, hydrogels that are elastic but still rigid containing 60-85% of water, and hydrogels that are soft and very elastic containing 85-99% of water. Hydrogels can be prepared from natural or synthetic polymers. Hydrogel-forming polymers are polymers that are capable of absorbing a substantial amount of water to form an elastic or inelastic gel. Examples of synthetic polymers are polyethylene oxide, poly(2-acrylamido-2-methyl-1-propanesulfonic acid), polyvinylpyrrolidone, polyacrylamides, polyvinyl alcohol, sodium polyacrylate, acrylate polymers and copolymers with an abundance of hydrophilic groups. Examples of natural polymers and their derivatives are polysaccharides such as dextrin, dextran, chitin, chitosan, carrageenan and agar, cellulose and its derivatives, alginate, natural gums such as xanthan gum, locust bean gum, and collagen and its derivatives such as gelatin.

During the method of preparation of a controlled release composition as described above, at least one therapeutic protein is present before and during the cross-linking process and will therefore be enclosed in the three-dimensional network formed by the chemically cross-linked gelatin. Examples of proteins which can be incorporated into the drug delivery device of the present invention include, but are not limited to, hemoglobin, vasporessin, oxytocin, adrenocorticocotrophic hormone, epidermal growth factor, prolactin, luliberin or luteinising hormone releasing factor, human growth factor, basic fibroblast growth, hepatocyte growth factor, angiogenesis growth factor, vascular endothelial growth factor, bone morphogenetic growth factor, nerve growth factor, and the like; interleukines, enzymes such as adenosine deaminase, superoxide dismutase, xanthine oxidase, and the like; enzyme systems; blood clotting factors; clot inhibitors or clot dissolving agents such as streptokinase and tissue plasminogen activator; antigens for immunization; hormones.

The gelatin used in a controlled release composition of the invention can be selected from a vast array of gelatins, and are made with recombinant techniques. The gelatins used in aspects of the present invention preferably essentially completely consist of gelatine molecules having a molecular weight above 2.5 kD.

In principle every gelatin can be modified to fit the used therapeutic protein, for example by introducing certain charges in the gelatin to strengthen the binding of the used therapeutic protein to the controlled release composition. An example of a modified gelatin having quaternary ammonium groups is "Croquat™" gelatin produced by Croda Colloids Ltd. Gelatins that may be used as the starting point for modified gelatin may include any known gelatin, whether lime-processed or acid processed and can for instance be selected from the group of lime treated bone or hide gelatin of pig, cattle or fish, recombinant gelatin, or combinations thereof. For every therapeutic protein a suitable environment can thus be created. The use of a recombinant gelatin based controlled release composition together with a therapeutic protein as a pharmaceutical is the preferred embodiment of the present invention. Recombinant gelatins are particularly attractive as polymers for the development of protein delivery systems for several reasons. The biotechnological production eliminates the risk prion contaminations, which are possibly present in animal source gelatins. Recombinant gelatins have well defined molecular weights, determined by the gelatin gene that is expressed. Furthermore, recombinant DNA technology opens the possibility to manipulate the amino acid sequence of gelatins. This is potentially useful for defining the number and the positions of amino acids involved in cross-linking, or for steering the biodegradability of gelatins by introducing amino acid sequences that are substrates (cleavage sites) for proteases.

For most pharmaceuticals a slow and gradual release is preferred wherein the release is at a more or less constant rate for a period of time, preferably ranging from several days to several weeks or even months. One of the main problems of currently used gelatin based controlled release compositions is that the release of enclosed pharmaceutical is typically preceded by a burst release of said pharmaceutical. This phenomenon is to a large extent governed by two parameters. One is the method of incorporation of the pharmaceutical into a controlled release matrix. The methods in the prior art describe that a controlled release matrix is first established by cross-linking. After cross-linking pharmaceutical is added and allowed to diffuse into the controlled release matrix. Further treatment (e.g. changing the liquid content of the controlled release matrix), may entrap most of the pharmaceutical in the matrix. However, a fraction of said pharmaceutical will not be entrapped during preparation. Furthermore, during use of the controlled release composition the liquid content can change, freeing even more entrapped pharmaceutical. Therefore a fraction of said pharmaceutical will be able to rapidly diffuse into it surroundings resulting in a burst release. The method for preparing the controlled release composition of the invention, however, cross-links the matrix in presence of the pharmaceutical causing genuine entrapment during crosslinking diminishing the unwanted burst release. Another parameter that governs the release characteristics of the controlled release matrix is the mesh size of the matrix. The average mesh size ($\xi$) of the gelatin matrix is the average 'pore size' of the entangled/cross-linked gelatin network at physiological conditions (pH 7.4, 37° C., 300 mOsm/L). If a release is diffusion controlled the rate of release is relatively fast, usually in a timescale of hours. In case a slow release is desired the matrix of the hydrogel preferably should be more restrictive in respect to the pharmaceutical component. Most preferred is the condition that the release is mainly governed by degradation of the matrix.

The terms "entrap" or "entrapped" as used herein refer to the fact that the pharmaceutical is held captured (in a space defined) by individually crosslinked gelatin molecules. This term is different from the term "encapsulated", wherein the pharmaceutical is contained in a location that is surrounded, enclosed or enveloped by the encapsulating material.

The rate at which the pharmaceutical is released from the controlled release composition of the present invention (i.e. the release rate) is such that preferably less than 50%, more preferably less than 40%, even more preferably less than 30%, 20%, 10%, 5%, 4%, 3%, 2% or 1% of the fraction of the pharmaceutical entrapped in the controlled release composition is released in a period of 24 hours when the controlled release composition is placed in aqueous solution (for instance as described in the Examples). Such slow release rates are indicative of degradation-governed release, rather than diffusion-governed release.

In the release of a pharmaceutical such as a protein from the matrix the phenomenon known as diffusion plays an important role. For a particle which can be a single molecule, a polymer, a complex, an aggregate or any other form of pharmaceutical, from the diffusion coefficient the hydrodynamic radius can be calculated via the Stokes-Einstein equation in which the radius by strict definition is that of a hypothetical hard sphere that diffuses with the same speed as the particle under consideration. It is more correct to say that this radius is indicative of the apparent size of the dynamic hydrated solvated particle which in this invention is a pharmaceutical.

A suitable method for determining the hydrodynamic radius is dynamic light scattering (DLS). For instance for a protein as lysozyme a value of 1.90 nm has been measured. In the current invention the hydrodynamic radius is preferably measured at physiological conditions.

In a preferred embodiment, the invention provides a controlled release composition comprising a cross-linked gelatin and at least one therapeutic protein wherein the ratio of the average mesh size ($\xi$) of the gelatin matrix and the average hydrodynamic radius ($R_H$) of said therapeutic protein is smaller than 2, preferably smaller than 1.5, most preferably smaller than 1.

The preferred mesh size thus depends on the hydrodynamic radius of the therapeutic protein. Without being bound by theory it is imagined by the inventor that for ratios of average mesh size and average hydrodynamic radius smaller than 2 diffusion gradually becomes less influential and for ratios smaller than 1 biodegradation is expected to be the main mechanism of release. Very small mesh sizes corresponding to high cross-linking densities are thought not to be required for achieving a slow release but on the other hand form most likely no functional disadvantage assuming that the therapeutic protein is incorporated in the hydrogel structure simultaneously with the cross-linking reaction. There is no functional lower limit for the ratio of average mesh size and average hydrodynamic radius. Practically the mesh size obtainable is limited by the number of cross-linkable places in the gelatin molecule and also depends on the conditions of measurement. Preferably the relevant parameters are determined at physiological conditions.

The average mesh size is determined by the elasticity of the matrix which may be determined by for instance dynamic mechanical analysis (DMA). Dynamic mechanical analysis (DMA) of hydrogels in the equilibrium swollen state is, for example, performed with a DMA 2980 dynamic mechanical analyzer (TA Instruments, New Castle, Del.), equipped with a liquid filled sample holder for preventing water evaporation from hydrogels, and operating at 37° C.

Without being bound by theory it is thought that in normal, conventionally isolated gelatins always a certain fraction of low molecular weight peptides (more specifically below 2.5 kD) is present. It is very difficult to control the cross-linking of these peptides into the gelatin matrix. As a result hydrogels of natural derived gelatins lack homogeneity with respect to the spaces in the gelatin network. Parts will be densely cross-linked while other parts with a high concentration of peptides will be less cross-linked. In these networks loosely cross-linked regions will be present for which the mesh size ($\xi$) of the hydrogel is substantially greater than the hydrodynamic radius ($R_H$) of the therapeutic protein contained in the gel (both defined under physiological pH- and salt-conditions). In these regions the motion and release of the therapeutic protein is governed by diffusion. As the release by diffusion is much faster (time scale hours) than the release by biodegradation (time scale weeks) the peptide rich inhomogeneous networks result in unintentional and unwanted premature release of at least part of the therapeutic protein, i.e. there is an unintentional and unwanted initial burst of enclosed pharmaceutical.

Recently, protein polymers like gelatin and collagen that were originally natural derived are also produced biotechnologically by the use of recombinant DNA technology. In one embodiment recombinant gelatins are produced using a yeast as an expression system. Yeast cells can be selected from *Hansenula, Trichoderma, Aspergillus, Penicillium, Saccharomyces, Kluyveromyces, Neurospora, Arxula* or *Pichia*. Methylotrophic yeast hosts are most preferred. Examples of methylotrophic yeasts include strains belonging to *Hansenula* or *Pichia* species. Preferred species include *Hansenula polymorpha* and *Pichia pastoris*. The recombinant gelatins used in aspects of the invent ton are preferably non-hydroxylated. In conventional gelatine proline and lysine residues may be hydroxylated. Hydroxylated gelatine are known to form secondary and triple helix structures, this may have detrimental effects on homogeneity of hydrogels prepared from them. The recombinant gelatines of invention are therefore preferably non-hydroxylated. The recombinant gelatine of the invention is preferably non-glycosylated. Glycosylation of protein is known to have a detrimental affect on their immunogenicity, which is unwanted for a composition for medical use. As a consequence of the numerous possible differences between non-recombinant and recombinant gelatins, the latter should be regarded as a new class of biopolymers.

Recombinant gelatin (also referred to as recombinant collagen or recombinant collagen-like peptides) typically refers to one or more gelatin or gelatin-like polypeptides produced by recombinant methods, such as by expression of a nucleotide encoding the peptide in a micro-organism, insect, plant or animal host. Such peptides are characterized by comprising Gly-Xaa-Yaa triplets wherein Gly is the amino acid glycine and Xaa and Yaa can be the same or different and can be any known amino acid. At least 40% of the amino acids are preferably present in the form of consecutive Gly-Xaa-Yaa triplets. More preferably at least 60%, even more preferably at least 80% or even more than 90% of the amino acids are present in the form of Gly-Xaa-Yaa triplets. Preferably, the peptides have a molecular weight of about 2.5 kD or more. More preferred are molecular weights of between about 2.5 to about 100 kD or between about 5 to about 90 kD. Molecular weights of less than 2.5 kD are not preferred because such molecules do generally not contain enough cross-linkable groups sufficient for obtaining a hydrogel with a desired structure. Also preferred are molecular weights of recombinant gelatin of about 60 kD or less, preferably between about 5 and about 50 kD, more preferably between about 7 and about 40 kD. Recombinant gelatin can be produced as described in EP-A-0926543 and EP-A-1014176 or as described in U.S. Pat. No. 6,150,084.

Recombinant gelatins can for example be derived from any type of collagen, such as collagen type I, II, III, or IV. In a preferred embodiment the recombinant gelatins are derived or designed from mammalian (preferably human) collagens to avoid potential adverse immunogenic responses. In other examples the recombinant gelatin might be designed to meet specific application needs with respect to interaction with the tissue in which the hydrogel is placed. For example recombinant gelatins might be enriched in RGD motifs (i.e. arginine-glycine-aspartic acid sequence). RGD motives in proteins are well known to affect and enhance cell-binding properties.

There are different ways in which a solution of a (recombinant) gelatin and a pharmaceutical can be prepared. For example, one can first prepare a solution of a (recombinant) gelatin by dissolving a recombinant gelatin in a suitable solvent and subsequently adding or dissolving a pharmaceutical to or in the prepared recombinant gelatin solution. Aqueous solutions are most preferred. Mixtures with water miscible organic solvents such as tetrahydrofurane, acetone or ethanol can also be used. Other solvents that may be applied are glycol, tetrafluorethane, dimethylsulfoxide, N,N-dimethylformamide, and N-Methyl-Pyrrolidinone (NMP). All solvents can be used alone or as mixture with other solvents. In some cases a specific pH is required, for example to steer the electrostatic interaction between the gelatin matrix and the pharmaceutical. The pH can be adjusted using any acid or base. Furthermore solutions can be buffered using all commonly known organic or inorganic buffers. It is clear that if the (recombinant) gelatin is already present as a solution the first part of this example can be skipped or replaced by diluting said recombinant gelatin in a suitable diluent. In another example one first prepares a solution of a pharmaceutical by adding or dissolving said pharmaceutical to or in a suitable diluent or solvent and subsequently adding or dissolving a recombinant gelatin to or in the solution comprising said pharmaceutical. In yet another example, one adds and/or dissolves a (recombinant) gelatin and a pharmaceutical at the same time to or in a suitable diluent or solvent.

The pharmaceutical does not always need to be dissolved. In case the solubility of the pharmaceutical in the solvent system used is limited it is also possible to use particle suspensions of the pharmaceutical. These particle suspensions can be already preformed and added to the gelatin solution or vice versa, or be formed, i.e. precipitated, in the gelatin solution.

An important feature of controlled release compositions is, that the polymer used in the hydrogel formation should be biodegradable and as such does not require invasive surgical methods to be removed after complete release of pharmaceuticals. Moreover biodegradability could be required to release the pharmaceutical used in the composition. A priori it is not obvious whether recombinant gelatins will be broken down by the same mechanisms causing degradation of natural gelatins. It is known that natural gelatins and collagens are degraded in the human body by proteases and more specifically matrix-metalloproteinases (MMP). Matrix metalloproteinases (MMP's) are zinc-dependent endopeptidases. The MMP's belong to a larger family of proteases known as the metzincin superfamily. Collectively they are capable of degrading all kinds of extracellular matrix proteins, but also can process a number of bioactive molecules. An important group of MMP's are the collagenases. These MMP's are capable of degrading triple-helical fibrillar collagens into distinctive ¾ and ¼ fragments. These collagens are the major components of bone and cartilage, and MMP's are the only known mammalian enzymes capable of degrading them. Traditionally, the collagenases are: MMP-1 (Interstitial collagenase), MMP-8 (Neutrophil collagenase), MMP-13 (Collagenase 3) and MMP-18 (Collagenase 4). Another important group of MMP's is formed by the gelatinases. The main substrates of these MMP's are type IV collagen and gelatin, and these enzymes are distinguished by the presence of an additional domain inserted into the catalytic domain. This gelatin-binding region is positioned immediately before the zinc binding motif, and forms a separate folding unit which does not disrupt the structure of the catalytic domain. The two members of this sub-group are: MMP-2 (72 kDa gelatinase, gelatinase-A) and MMP-9 (92 kDa gelatinase, gelatinase-B).

In a preferred embodiment, the invention provides a controlled release composition comprising a cross-linked gelatin and at least one therapeutic protein wherein the ratio of the average mesh size ($\xi$) of the gelatin matrix and the average hydrodynamic radius ($R_H$) of said therapeutic protein is smaller than 2, preferably smaller than 1.5, in which said gelatin is recombinant gelatin.

In an especially preferred embodiment, the invention provides a controlled release composition comprising a cross-linked recombinant gelatin and at least one therapeutic protein wherein the ratio of the average mesh size ($\xi$) of the gelatin matrix and the average hydrodynamic radius of said therapeutic protein is smaller than 2, preferably smaller than 1.5, in which said recombinant gelatin is human or human-like. Human-like gelatin is defined as being for at least 60%, more preferable for at least 80%, most preferably for at least 90% identical to amino acid sequence of gelatin in human collagen. A starting point for preparing a recombinant human or human-like gelatin is for example the human Col1A1 sequence. However, it is also possible to use other human collagen sequences to start with. Recombinant human gelatin is defined herein as gelating having a human amino acid sequence, a level of glycosylation equal to human gelatin as well as a level of hydroxylation equal to the human gelatin. Human-like gelatin refers to recombinant gelatin having one or more mutations in the amino acid sequence of the protein, an altered level of glycosylation relative to endogenous human levels (preferably lowered in order to reduce immunogenicity of the recombinant gelatin), and/or altered level of hydroxuylation of lysine and/or proline residues relative to endogenous human levels. Mammalian-like is the corresponding term for mammalian-derived gelatins.

The recombinant gelatin used in a method of the invention can be selected from a vast array of recombinant gelatins, for example a recombinant gelatin based on human collagen type I, II, III, or IV. As described above, a recombinant gelatin can be produced in any suitable (over)expression system, for example expression in yeast, bacteria, fungi or plants. It is clear to the skilled person that the use of a certain expression system might impose specific properties on the produced recombinant gelatin, for example a different glycosylation pattern (if compared to a natural variant) or no glycosylation at all.

An important advantage of the use of a recombinant gelatin is that well-defined controlled release compositions can be prepared. Also the constant quality (for example the purity and well-defined molecular weight) of the recombinant gelatins compared to animal derived gelatins contributes to the preservation of the quality of the pharmaceutical in the controlled release composition.

Another important advantage of a recombinant gelatin is that the amino acid sequence can be manipulated to create certain characteristics. Examples of characteristics that can now be manipulated are (i) the amount of cross-linkable amino acids (for example the amount of (hydroxy)lysines), (ii) the glycosylation pattern (for example the absence of threonine and/or serine amino acids in certain triplets results in the absence of glycosylation), (iii) the size of the recombinant gelatin, (iv) the charge density of the recombinant gelatin can be amended (for example charged amino acids, such as asparagine (Asn), aspartic acid (Asd), glutamine (Gln), glutamic acid (Glu) or lysine (Lys) can be introduced or left out) and as such the loading and release of a pharmaceutical (especially a therapeutic protein) can be influenced or (v) the biodegradability can be amended by the presence or absence of cleavage sites for metalloproteases.

As mentioned above one important characteristic of a recombinant gelatin is the amount of cross-linkable amino acids, such as the amount of (hydroxy)-lysine groups and the amount of carboxylic acid groups derived from aspartic and glutamic acid.

In a preferred embodiment, the invention provides a controlled release composition comprising a cross-linked (recombinant) gelatin and at least one therapeutic protein wherein the ratio of the average mesh size ($\xi$) of the gelatin matrix and the average hydrodynamic radius of said therapeutic protein is smaller than 2, preferably smaller than 1.5, wherein said (recombinant) gelatin comprises at least 0.05 mmol/g (hydroxy)lysine groups. Preferably said recombinant gelatin comprises at least 0.10 mmol/g lysine or hydroxylysine groups, more preferably at least 0.20 mmol/g to obtain a suitable structure after cross-linking. Also higher lysine or hydroxylysine contents of around 0.40 or up to 0.60 or 0.80 mmol/g may be applied depending on the desired three dimensional network structure.

It is clear that the amount of cross-linkable group has an effect on the degree of cross-linking. If more cross-linkable groups are available, the amount of cross links can in principle be higher if compared to a situation in which less linkable groups are present. The lower limit of cross-linkable groups is that amount that still can result in the formation of a gel. The amount of cross-linkable groups in principle also determines the mesh size which is a measure of the average "pore size" of the entangled/cross-linked gelatin network at physiological conditions (pH 7.4, 37° C. and 300 mOsm/L). Finally, the amount of cross-linked groups determines the biodegradability of the formed controlled release composition. By using a recombinant gelatin the amount of cross-linkable groups can be influenced and thus the gel mesh size and biodegradability can be manipulated.

Depending on the application the controlled release composition can be obtained as a gel or elastic semi-solid in various shapes by pouring it in molds and subsequent (chemical) cross-linking. Furthermore controlled release particles may be obtained by emulsifying the controlled release composition and isolating the formed emulsion droplets after cross-linking as more or less solid particles. Another way to obtain controlled release particles is by spray drying. Particle size may range from 0.1 micrometer to 1000 micrometer, but depending on the application and the desired release profile, more specific ranges could be selected. In case injectable formulations are used the particle size preferably should not exceed 200 micrometer. Furthermore the controlled release compositions may be cast into films or sheets. Examples of suitable casting techniques include spin coating, gravure coating, flow coating, spray coating, coating with a brush or roller, screen printing, knife coating, curtain coating, slide curtain coating, extrusion, squeegee coating, and the like. Film or sheet thickness may range from 1 micrometer up to 1 centimeter. For example in case of wound dressings thicknesses of 1 millimeter to 1 centimeter are preferred, while for coatings of medical devices such as stents or vascular grafts or other implants coating thicknesses up to 1 mm are preferable. Drying of the compositions may be performed by common techniques such as air drying, vacuum drying, freeze drying, or spray drying.

Depending on for example the stability of the used pharmaceutical during the process of cross-linking it may also be possible to first prepare the cross-linked hydrogel and optionally dry it in the absence of the pharmaceutical and then include the pharmaceutical. Upon cross-linking of the matrix the therapeutic protein (TP) can be co-cross-linked resulting in activity loss and in worst-case toxic effects. Hence it has advantages to incorporate the TP after preparing the hydrogel. Several techniques may be applied to incorporate the pharmaceutical in the (dried) hydrogel such as submersing the (dried) hydrogel in solution of a pharmaceutical or by dripping solution of the pharmaceutical on top.

In case of chemical cross-linking, the recombinant gelatin is for example provided with a (chemical) linker and subsequently subjected to a linking reaction. The invention therefore provides a controlled release composition comprising a chemically cross-linked gelatin and at least one therapeutic protein wherein the ratio of the average mesh size ($\xi$) of the gelatin matrix and the average hydrodynamic radius of said therapeutic protein is smaller than 2, preferably smaller than 1.5, wherein said gelatin is chemically modified with a cross-linkable group.

Said cross-linkable group may be selected from, but is not limited to epoxy compounds, oxetane derivatives, lactone derivatives, oxazoline derivatives, cyclic siloxanes, or ethenically unsaturated compounds such as acrylates, methacrylates, polyene-polythiols, vinylethers, vinylamides, vinylamines, allyl ethers, allylesters allylamines, maleic acid derivatives, itacoic acid derivatives, polybutadienes and styrenes. Preferably as the cross-linkable group (meth)acrylates are used, such as alkyl-(meth)acrylates, polyester-(meth)acrylates, urethane-(meth)acrylates, polyether-(meth)acrylates, epoxy-(meth)acrylates, polybutadiene-(meth)acrylates, silicone-(meth) acrylates, melamine-(meth)acrylates, phosphazene-(meth)acrylates, (meth)acrylamides and combinations thereof because of their high reactivity. Even more preferably said cross-linkable group is a methacrylate and hence the invention also provides methacrylated (recombinant) gelatin. Such a methacrylated (recombinant) gelatin is very useful in the preparation of a controlled release composition. Generally, the linking groups (for example methacrylate) are coupled to the (recombinant) gelatin and cross-linking is obtained by redox polymerisation (for example by subjection to a chemical initiator such as the combination potassium peroxodisulfate (KPS)/N,N,N',N' tetramethylethyenediamine (TEMED)) or by radical polymerisation in the presence of an initiator for instance by thermal reaction of by radiation such as UV-light).

Photo-initiators may be used in accordance with the present invention and can be mixed into the solution of the recombinant gelatin. Photo-initiators are usually required when the mixture is cured by UV or visible light radiation. Suitable photo-initiators are those known in the art such as radical type, cation type or anion type photo-initiators.

Examples of radical type I photo-initiators are α-hydroxyalkylketones, such as 2-hydroxy-1-[4-(2-hydroxyethoxy)phenyl]-2-methyl-1-propanone (Irgacure™ 2959: Ciba), 1-hydroxy-cyclohexyl-phenylketone (Irgacure™ 184: Ciba), 2-hydroxy-2-methyl-1-phenyl-1-propanone (Sarcure™ SR1173; Sartomer), oligo[2-hydroxy-2-methyl-1-{4-(1-methylvinyl)phenyl}propanone] (Sarcure™ SR1130: Sartomer), 2-hydroxy-2-methyl-1-(4-tert-butyl-)phenylpropan-1-one, 2-hydroxy-[4'-(2-hydroxypropoxy)phenyl]-2-methylpropan-1-one, 1-(4-isopropylphenyl)-2-hydroxy-2-methyl-propanone (Darcure™ 1116: Ciba); α-aminoalkylphenones such as 2-benzyl-2-(dimethylamino)-4'-morpholinobutyrophenone (Irgacure™ 369; Ciba), 2-methyl-4'-(methylthio)-2-morpholinopropiophenone (Irgacure™ 907: Ciba); α,α-dialkoxyacetophenones such as α,α-dimethoxy-α-phenylacetophenone (Irgacure™ 651: Ciba), 2,2-diethyoxy-1,2-diphenylethanone (Uvatone™ 8302: Upjohn), α,α-diethoxyacetophenone (DEAP: Rahn), α,α-di-(n-butoxy)acetophenone (Uvatone™ 8301: Upjohn); phenylglyoxolates such as methylbenzoylformate (Darocure™ MBF: Ciba); benzoin derivatives such as benzoin (Esacure™ BO: Lamberti), benzoin alkyl ethers (ethyl, isopropyl, n-butyl, iso-butyl, etc.), benzylbenzoin benzyl ethers, Anisoin; mono- and bis-Acylphosphine oxides, such as 2,4,6-trimethylbenzoyl-diphenylphosphine oxide (Lucirin™ TPO; BASF), ethyl-2,4,6-trimethylbenzoylphenylphosphinate (Lucirin™ TPO-L: BASF), bis(2,4,6-trimethylbenzoyl)-phenylphosphine oxide (Irgacure™ 819; Ciba), bis(2,6-dimethoxybenzoyl)-2,4,4-trimethyl-pentylphosphineoxide (Irgacure 1800 or 1870). Other commercially available photo-initiators are 1-[4-(phenylthio)-2-(O-benzoyloxime)]-1,2-octanedione (Irgacure OXE01), 1-[9-ethyl-6-(2-methylbenzoyl)-9H-carbazol-3-yl]-1-(O-acetyloxime)ethanone (Irgacure OXE02), 2-hydroxy-1-{4-[4-(2-hydroxy-2-methyl-propionyl)-benzyl]- phenyl}-2-methyl-propan-1-one (Irgacure127), oxy-phenyl-acetic acid 2-[2 oxo-2-phenyl-acetoxy-ethoxy]-ethyl ester (Irgacure754), oxy-phenyl-acetic-2-[2-hydroxy-ethoxy]-ethyl ester (Irgacure754), 2-(dimethylamino)-2-(4-methylbenzyl)-1-[4-(4-morpholinyl)phenyl]-1-butanone (Irgacure 379), 1-[4-[4-benzoylphenyl)thio]phenyl]-2-methyl-2-[(4-methylphenyl)sulfonyl)]-1-propanone (Esacure 1001M from Lamberti), 2,2'-bis(2-chlorophenyl)-4,4',5,5'-tetraphenyl-1,2'-bisimidazole (Omnirad BCIM from IGM).

Examples of type II photo-initiators are benzophenone derivatives such as benzophenone (Additol™ BP: UCB), 4-hydroxybenzophenone, 3-hydroxybenzophenone, 4,4'-dihydroxybenzophenone, 2,4,6-trimethylbenzophenone, 2-methylbenzophenone, 3-methylbenzophenone, 4-methylbenzophenone, 2,5-dimethylbenzophenone, 3,4-dimethylbenzophenone, 4-(dimethylamino)benzophenone, [4-(4-methylphenylthio)phenyl]phenyl-methanone, 3,3'-dimethyl-4-methoxy benzophenone, methyl-2-benzoylbenzoate, 4-phenylbenzophenone, 4,4-bis(dimethylamino)benzo-phenone, 4,4-bis(diethylamino)benzophenone, 4,4-bis(ethylmethylamino)benzo-phenone, 4-benzoyl-N,N,N-trimethyl-benzenemethanaminium chloride, 2-hydroxy-3-(4-benzoylphenoxy)-N,N, N-trimethyl-1-propanamium chloride, 4-(13-Acryloyl-1,4,7,10,13-pentaoxamidecyl)benzophenone (Uvecryl™ P36: UCB), 4-benzoyl-N,N-dimethyl-N-[2-(1-oxo-2 propenyl)oy]ethylbenzene-methanaminium chloride, 4-benzoyl-4'-methyldiphenyl sulphide, anthraquinone, ethylanthraquinone, anthraquinone-2-sulfonic acid sodium salt, dibenzosuberenone; acetophenone derivatives such as acetophenone, 4'-phenoxyacetophenone, 4'-hydroxyacetophenone, 3'-hydroxyacetophenone, 3'-ethoxyacetophenone; thioxanthenone derivatives such as thioxanthenone, 2-chlorothioxanthenone, 4-chlorothioxanthenone, 2-isopropylthioxanthenone, 4-isopropylthioxanthenone, 2,4-dimethylthioxanthenone, 2,4-diethylthioxanthenone, 2-hydroxy-3-(3,4-dimethyl-9-oxo-9H-thioxanthon-2-yloxy)-N,N,N-trimethyl-1-propanaminium chloride (Kayacure™ QTX: Nippon Kayaku); diones such as benzyl, camphorquinone, 4,4'-dimethylbenzyl, phenanthrenequinone, phenylpropanedione; dimethylanilines such as 4,4,4"-methylidyne-tris(N,N-dimethylaniline) (Omnirad™ LCV from IGM); imidazole derivatives such as 2,2'-bis(2-chlorophenyl)-4,4',5,5'-tetraphenyl-1,2'-bisimidazole; titanocenes such as bis(eta-5-2,4-cyclopentadiene-1-yl)-bis-[2,6-difluoro-3-1H-pyrrol-1-yl]phenyl]titanium (Irgacure™784: Ciba); iodonium salt such as Iodonium, (4-methylphenyl)-[4-(2-methylpropyl-phenyl)-hexafluorophosphate (1-). If desired combinations of photo-initiators may also be used.

For acrylates, diacrylates, triacrylates or multifunctional acrylates, type I photo-initiators are preferred. Especially alpha-hydroxyalkylphenones, such as 2-hydroxy-2-methyl-1-phenyl propan-1-one, 2-hydroxy-2-methyl-1-(4-tert-butyl-) phenylpropan-1-one, 2-hydroxy-[4'-(2-hydroxypropoxy)phenyl]-2-methylpropan-1-one, 2-hydroxy-1-[4-(2-hydroxyethoxy)phenyl]-2-methyl propan-1-one, 1-hydroxycyclohexylphenylketone and oligo[2-hydroxy-2-methyl-1-{4-(1-methylvinyl)phenyl}propanone], alpha-aminoalkylphenones, alpha-sulfonylalkylphenones and acylphosphine oxides such as 2,4,6-trimethylbenzoyl-diphenylphosphine oxide, ethyl-2,4,6-trimethylbenzoyl-phenylphosphinate and bis(2,4,6-trimethylbenzoyl)-phenylphosphine oxide, are preferred.

Cross-linking by infrared radiation is also known as thermal curing. Thus cross-linking may be effectuated by combining the ethylenically unsaturated groups with a free radical initiator and optionally a catalyst and heating the mixture. Exemplary free radical initiators are organic peroxides such as ethyl peroxide and benzyl peroxide; hydroperoxides such as methyl hydroperoxide, acyloins such as benzoin; certain azo compounds such as α,α'-azobisisobutyronitrile and γ,γ'-azobis(γ-cyanovaleric acid); persulfates; peroxosulfates; peracetates such as methyl peracetate and tert-butyl peracetate; peroxalates such as dimethyl peroxalate and di(tert-butyl) peroxalate; disulfides such as dimethyl thiuram disulfide and ketone peroxides such as methyl ethyl ketone peroxide. Temperatures in the range of from about 23° C. to about 150° C. are generally employed. More often, temperatures in the range of from about 37° C. to about 110° C. are used.

When selecting a cross-linking method it is of high importance to verify that the therapeutic protein is not 'damaged' by the reaction and maintains its therapeutic activity.

The use of methacrylated gelatin is especially preferred in combination with a therapeutic protein, because cross-linking of methacrylated gelatin can be performed in the presence of a therapeutic protein without co-cross-linking the therapeutic protein.

As a result of cross-linking, a controlled release composition comprising a pharmaceutical is obtained. The mesh size or pore size of the obtained product is dependent on the used (recombinant) gelatin and the cross-linking density. The mesh size is defined as the average distance between two neighbouring cross-links in the hydrogels polymer network. If a therapeutic protein is used as a pharmaceutical, the mesh size can be both larger and smaller than the hydrodynamic radius of the therapeutic protein. The hydrodynamic radius $R_H$ is the apparent radius of a protein in the gelatin matrix taken into account all environmental effects. As such the hydrodynamic radius is derived from the diffusion coefficient D via the relation $D=kT/6\pi\eta R_H$, in which k is Boltzmann's constant, T is the temperature in Kelvin, π is 3.14, and η is the viscosity of the solution in mPa·s. In the current invention the hydrodynamic radius is preferably measured at physiological conditions. The speed of degradation of the obtained product depends on the amount of cross-links: the more cross-links the slower the degradation. In a preferred embodiment, the speed of degradation is within one year. As release profiles of pharmaceuticals usually extend to a couple of weeks or maximally a few months it is preferable that the matrix consisting of (recombinant) gelatin degrades in a similar time window. The final charge density of the obtained product depends both on the used amino acid sequence of the recombinant gelatin as well as on the degree of cross-linking. The obtained product can have different appearances, for example dense/homogenous or macroporous. The release profile of the used pharmaceutical can be from several hours (diffusion controlled) to weeks or months (controlled by degradation speed). A combination of both mechanisms can also occur. For most applications a slow release is preferred and hence biodegradation as main mechanism.

As described, the cross-linking can be obtained by cross-linking (meth)acrylate residues introduced in the pre-modification of the recombinant gelatin. However, it is also possible to use a chemical cross-linker that does not need a separate coupling to the used recombinant gelatin. In another embodiment, the invention provides a method for preparing a controlled release composition comprising the steps of:

providing a solution of a recombinant gelatin and a pharmaceutical cross-linking said recombinant gelatin to obtain a three dimensional structure, wherein said cross-linking is obtained by using a chemical cross-linker selected from water soluble carbodiimide, non-soluble carbodiimide, di-aldehyde di-iso-cyanate, aldehyde compounds such as formaldehyde and glutaraldehyde, ketone compounds such as diacetyl and chloropentanedion, bis (2-chloroethylurea), 2-hydroxy-4,6-dichloro-1,3,5-triazine, reactive halogen-containing compounds disclosed in U.S. Pat. No. 3,288,775, carbamoyl pyridinium compounds in which the pyridine ring carries a sulphate or an alkyl sulphate group disclosed in U.S. Pat. No. 4,063,952 and U.S. Pat. No. 5,529,892, divinylsulfones, and the like. S-triazine derivatives such as 2-hydroxy-4,6-dichloro-s-triazine are well known cross-linking compounds.

Basically the cross-linking occurs between two reactive groups on different gelatin molecules. Particularly preferred is the use of water soluble carbodiimide 1-(3-Dimethylaminopropyl)-3-ethylcarbodiimide hydrochloride.

Depending on the type of gelatin (the number of cross-linkable groups) and the method of cross-linking selected a certain cross-link density can be obtained which is strongly related to the average mesh size that can be achieved When a cross-linking group is coupled to the gelatin in a separate step and for the hydrogel a dense structure is desired it is preferred that at least 50% of the cross-linkable groups in the gelatin are activated, more preferably at least 75%. Most preferably the degree of substitution is close to 100%.

All kinds of pharmaceuticals can be incorporated in the controlled release composition. The term "pharmaceutical" refers to chemical or biological molecules providing a therapeutic, diagnostic, or prophylactic effect preferably in vivo. The term pharmaceutical is also meant to indicate prodrug forms thereof A "prodrug form" of a pharmaceutical means a structurally related compound or derivative of the pharmaceutical which, when administered to a host is converted into the desired pharmaceutical. A prodrug form may have little or none of the desired pharmacological activity exhibited by the pharmaceutical to which it is converted.

Examples of proteins which can be incorporated into the drug delivery device of the present invention include, but are not limited to, hemoglobin, vasporessin, oxytocin, adrenocorticocotrophic hormone, epidermal growth factor, prolactin, luliberin or luteinising hormone releasing factor, human growth factor, basic fibroblast growth, hepatocyte growth factor, angiogenesis growth factor, vascular endothelial growth factor, bone morphogenetic growth factor, nerve growth factor, and the like; interleukins; enzymes such as adenosine deaminase, superoxide dismutase, xanthine oxidase, and the like; enzyme systems; blood clotting factors; clot inhibitors or clot dissolving agents such as streptokinase and tissue plasminogen activator; antigens for immunization; hormones.

The controlled release composition may comprise at least one kind/type of (recombinant) gelatin but can also be performed by using at least two kinds/types of (recombinant) gelatin preferably with different characteristics). Moreover, combinations of a gelatin with at least one water-soluble polymer (preferably biodegradable potentially cross-linking and not being a gelatin) are also possible. Without limiting the scope of the above invention these biodegradable polymers can be natural or synthetic or made by recombinant techniques. Examples are dextrans, hyaluronic acid, poly-lactic acid, poly-glycolic acid, or copolymers of those, chitin, chitosan, alginate, polyesters, etc. Further suitable polymers are disclosed in US 2004/0235161 on pg 2. Also the amount of cross-linkers can be varied from at least one or at least two to more than two (for example three or four).

It is an aspect of the present invention that the controlled release compounds are essentially homogeneous with respect to cross-linking, and do not exhibit burst release characteristics, which are diffusion-governed and which coincide with release rates wherein over 50% of the pharmaceutical is released from the cross-linked gelatine matrix within 24 hours when tested under the conditions as described in the experimental part.

Furthermore addition of adjuvants like buffers, salts, surfactants, humectants and co-solvents in the preparation process can also be used.

Also the amount and kinds of used pharmaceuticals can be varied, for example the use of at least two therapeutic proteins or the use of a therapeutic protein in combination with an antibiotic.

In yet another embodiment, the invention provides a method for preparing a controlled release composition as described herein, comprising selecting a therapeutic protein and optionally determining the hydrodynamic radius ($R_H$) of said protein selecting a (recombinant) gelatin which upon cross-linking under predetermined cross-linking conditions comprises mesh sizes smaller than 2 times the hydrodynamic radius ($R_H$) of said therapeutic protein; contacting said therapeutic protein with said (recombinant) gelatin;

cross-linking said (recombinant) gelatin under said under predetermined cross-linking conditions;

optionally purifying the obtained controlled release composition. Preferred predetermined cross-linking conditions are in principle experimentally determined by cross-linking the bare gelatin matrix and measuring the mesh size, and comparing it to the hydrodynamic radius of the therapeutic protein. However as a rule of thumb one can say that for gelatin concentrations of at least 20% in combination with at least a cross-linker amount of 0.3 mmol/g gelatin the diffusional release is reduced and release by biodegradation prevails. Preferably a gelatin concentration of 30% or more is used in combination with a cross-linker amount of at least 0.3 mmol/g gelatin, preferably at least 0.4 mmol/g gelatin.

The hydrogel can also be loaded after cross-linking and therefore the invention also provides a method for preparing a controlled release composition as described herein, comprising selecting a therapeutic protein and optionally determining the hydrodynamic radius ($R_H$) of said protein;

selecting a (recombinant) gelatin which upon cross-linking under predetermined cross-linking conditions comprises mesh sizes smaller than 2 times the hydrodynamic radius ($R_H$) of said therapeutic protein;

cross-linking said (recombinant) gelatin under said predetermined cross-linking conditions to obtain a controlled release composition;

contacting said therapeutic protein with said obtained controlled release composition structure under conditions that allows entry of said therapeutic protein into said controlled release composition;

optionally purifying the obtained controlled release composition.

The controlled release composition described herein can subsequently be used in the preparation of a pharmaceutical composition. In yet another embodiment, the invention thus provides a pharmaceutical composition comprising a controlled release composition, wherein said controlled release composition comprises at least a cross-linked (recombinant) gelatin and a therapeutic protein. Such a pharmaceutical composition can further comprise an adjuvant or diluent. Examples of suitable pharmaceutical compositions are an injectable formulation, a subdermal delivery depot, a dressing, or an implant (gel or moulded gel). An example of an injectable formulation is a formulation comprising (matrix) particles of 1-500 μm as described in EP 1 801 122.

The herein described controlled release composition can also be used in the preparation of a pharmaceutical article and the invention thus also provides a pharmaceutical article comprising a controlled release composition, wherein said controlled release composition comprises at least a cross-linked (recombinant) gelatin and a therapeutic protein. Examples of suitable articles are implants such as a stent or an artificial vascular graft, a bone implant or an insoluble drug particle, wound dressings, skin grafts.

A pharmaceutical composition according to the invention can be administered via any route, i.e. via injection (for example subcutaneous, intravenous or intramuscular) or via surgical implantation, orally, via inhalation or via an external wound dressing or even transdermal.

The invention further provides a method for treating a subject in need thereof, comprising providing said subject with an effective amount of a controlled release composition, i.e. a controlled release composition comprising at least a cross-linked (recombinant) gelatin and a therapeutic protein. Treatments that could be more effective using controlled release systems are for example: pain treatment, cancer therapy, cardiovascular diseases, myocardial repair, angiogenesis, bone repair and regeneration, wound treatment, neural stimulation/therapy, diabetics, and the like. The controlled release composition can be administered by injection (subcutaneous, intravenous or intramuscular) or orally or via inhalation. However, the used controlled release composition can also be implanted via surgery. Yet another suitable route of administering is via an external wound dressing or even transdermally.

The invention further provides use of a controlled release composition as described herein for the preparation of a medicament for the treatment of pain, cancer therapy, cardiovascular diseases, myocardial repair, angiogenesis, bone repair and regeneration, wound treatment, neural stimulation/therapy or diabetics.

The invention will be explained in more detail in the following, non-limiting examples.

Experimental Part

In the present invention, recombinant gelatins and natural gelatins were used for preparing hydrogels for the controlled release of proteins. In one embodiment methacrylate residues were coupled to recombinant gelatin to enable chemical cross-linking. The methacrylated gelatins were analyzed by $^1$H-NMR to determine the degree of substitution (DS), and by SDS-PAGE to determine purity. Hydrogels of methacrylated gelatins were formed by radical polymerization using potassium peroxodisulfate (KPS) and N,N,N',N'-tetramethylethylenediamine (TEMED) as initiators.

The release rate of the several 'therapeutic' proteins from the (recombinant) gelatin hydrogels as function of the mesh size as determined by the gelatin concentration and amount of crosslinks was studied.

Materials and Methods

Recombinant gelatins HU4 (MW 72.6 kDa), CBE (17.2 kDa), CBE3 (68 kDa) (a trimer of CBE), CBE5 (85 kDa) (a pentamert of CBE, and P4 (36.8 kDa) were used. The preparation of these recombinant gelatins is described elsewhere (EP-A-1398324, EP-A-0926543 and EP-A-1014176). FIGS. 1 to 4 show the amino acid sequence of these recombinant gelatins. These sequences are primarily based on human type I collagen while CBE and its trimer CBE 3 or its pentamer CBE5 contain an increased number of RGD motifs and an increased ratio of lysine amino acids. Furthermore as natural gelatins an acid treated hydrolysed porcine gelatin (average MW 26 kDa, polydispersity D 1.6, DGF Stoess and a hydrolysed alkali-treated bovine gelatin (average MW, 23 kDa, polydispersity D 1.6, Nitta) were used. Molecular weight and polydispersity were determined by GPC using a TSKgel superSW3000 and 2000 column with as eluens 10 mM $Na_2SO_4$, 1% SDS, pH 5.3.

Of the recombinant gelatins, CUBE (or a multimer thereof), in particular CBE3 or, CBE5, and P4 are preferred. Most preferred are, CBE3 and P4.

Methacrylic anhydride (MA-Anh) was purchased from Sigma-Aldrich (St. Louis, Mo.). Potassium peroxodisulfate (KPS) was obtained from Merck (Darmstadt, Germany). Stock solutions with 20 mg/ml KPS were prepared with isotonic phosphate buffer of pH 7.4, aliquoted in Eppendorf tubes, and stored at −20° C. N,N,N',N'-tetramethylethylenediamine (TEMED) was obtained from Fluka (Buchs, Switzerland). Stock solutions with 20% (v/v) TEMED were prepared in isotonic phosphate buffer of pH 7.4, aliquoted in Eppendorf tubes, and stored at −20° C. Proteins used were: egg hen lysozyme was obtained from Fluka (Buchs, Switzerland), Bovine Serum Albumin (BSA) from Sigma Aldrich, Netherlands. Stock solutions with 10 mg/ml protein, were prepared in isotonic phosphate buffer of pH 7.4, filtered through 0.2 mm HPLC filters (Alltech, Deerfield, Ill.), aliquoted in low binding Eppendorf tubes (Eppendorf, Hamburg, Germany), and stored at −20° C. Physiological phosphate buffer was prepared by dissolving 0.76 mg/ml $NaH_2PO_4 \times H_2O$, 0.79 mg/ml $Na_2HPO_4$, and 0.06 mg/ml NaCl, adjusting the pH to 7.4 with NaOH solution, and filtering the buffer solution through 0.2 mm filters (Schleicher und Schuell, Dassel, Germany).

TABLE I

| Type | Mw (kDa) | Number AA | Lysine amount | Lysine/1000 aa |
|---|---|---|---|---|
| HU4 | 72 | 821 | 32 | 39 |
| CBE | 17.2 | 192 | 11 | 57 |
| CBE5 | 85 | 900 | 56 | 60 |
| P4 | 36.8 | 401 | 12 | 30 |
| Pig skin gelatin | 26 | ~260 | 10 | 38 |
| Bone gelatin | 23 | ~230 | 9 | 40 | aa is 'amino acid'

A) Methacrylation of (Recombinant) Gelatin

Recombinant and natural gelatins were derivatized with methacrylate residues as follows. 2.5 g gelatin was dissolved in 200 ml phosphate buffer of pH 7.4. Solutions under a nitrogen atmosphere were heated to 50° C. and methacrylic-anhydride (MA-Anh) was added To achieve different degrees of substitution, the MA-Anh:gelatin ratio was varied. During the methacrylation reaction, the pH of the solution was regularly controlled and, if necessary, kept between 7 and 7.4 by the addition of 1 M NaOH solution. After vigorous stirring at 50° C. for one hour, the solutions were extensively dialyzed against water (dialysis tubes with 14 kDa MWCO Medicell International, London, UK). Dried products were obtained by lyophilization and were stored in sealed glass containers at 4° C.

B) Determination of Degree of Substitution (DS)

The actual degree of substitution (DS), i.e. the fraction of methacrylated amino acids with respect to the total number of primary amine groups of the recombinant gelatin, was determined by $^1$H-NMR. Measurements of were performed with a Gemini spectrometer (Varian Associates, Inc. NMR Instruments, Palo Alto, Calif.) operating at 300 MHz. Samples were prepared by dissolving 40 mg/ml gelatin in deuterium oxide. Forty scans were accumulated using a 62.5° pulse and 2 seconds relaxation delay. Integration of the phenylalanine signal and division of its area by the known number of phenylalanine protons gelatin molecule gave the area of one proton. Dividing the total area of the two methacrylate signals by the area of one proton gave the number of protons that made up the methacrylate signals. This value, divided by two, corresponded to the average number of methacrylate residues per gelatin chain and enabled the calculation of DS.

C) Preparation of Hydrogels Including Therapeutic Proteins

Hydrogels with an initial gelatin concentrations of 5, 10, 15, 20, 25, 30 and 40% (w/w) were prepared. Methacrylated gelatin was dissolved in phosphate buffer of pH 7.4 containing 0.05% NaN3, and solutions were centrifuged (5 min, 10000 RPM). Upon centrifugation, 596 mg gelatin solution was filled in an Eppendorf tube, and 75 μl phosphate buffer of pH 7.4 (or protein stock solution for release experiments) were added and gently mixed. KPS 20 mg/ml stock solution (56.5 μl) and TEMED 20% stock solution (22.5 μl) were added and mixed to induce cross-linking of the gelatin methacrylate residues. The solution was filled in 1 ml syringes (Becton-Dickinson, Franklin Lake, N.J.). After 1.5 h, the syringes were opened to remove the hydrogels, which were cut into cylinders of 6 mm length and 2.3 mm radius.

D) Mesh Size of the Hydrogels

Oscillatory shear experiments were performed using an AR 1000-N controlled stress rheometer (TA Instruments, New Castle, Del.) equipped with a stainless steal conical plate (40 mm diameter, 1° angle) and a solvent trap to prevent water evaporation from the sample. Hydrogel components were mixed as described above and pipetted on the rheometer. Gel formation at 20° C. was followed during 1.5 h by measuring the shear storage modulus (G') and the loss modulus (G"). G' and G" were also measured at 37° C. after gel formation was complete. The standard settings used for the measurements were a strain of 0.1% and an angular frequency of 6.283 rad/sec. To ensure that experiments were performed in the linear viscoelastic range, frequency sweep (0.6283-62.83 rad/sec) and strain sweep (0.05-2% strain) experiments were performed.

Dynamic mechanical analysis (DMA) of hydrogels in the equilibrium swollen state was performed with a DMA 2980 dynamic mechanical analyzer (TA Instruments, New Castle, Del.), equipped with a liquid filled sample holder for preventing water evaporation from hydrogels, and operating at 37° C. Experiments were conducted in the controlled force mode. The static force imposed on the hydrogels was increased from 0.001 to 0.95 N in 0.05 N steps. The stress in MPa that a hydrogel was subjected to was calculated from the static force and the known top surface area of the gel cylinder. The change of hydrogel height was used to calculate parameter α as a measure of strain:

$$\alpha = \frac{\Delta h}{h_{gel}} + 1 \quad (1')$$

where Δh is the change in hydrogel height and $h_{gel}$ is the original hydrogel height. The hydrogel elasticity modulus (E) was determined from the slope of stress against α (1).

E was used to determine the molecular weight between crosslinks ($M_c$): (2,3)

$$M_c = (3\rho RT)/E \quad (2')$$

where ρ is the gel density, R is the gas constant and T the absolute temperature in ° K.

Knowledge of $M_c$ enabled to estimate the average mesh size (ξ) of the hydrogels in the equilibrium swollen state using an equation that had been applied to non-recombinant gelatin hydrogels: (4)

$$\xi = 2\alpha' \left(\frac{M_c}{M_r}\right)^{1/2} \cdot (2.21 \text{ Å}) \cdot (Q_m)^{1/3} \quad (3')$$

Here, $M_r$ is the average molecular weight of one amino acid of the gelatin chain, and was estimated to be 100 g/mol. The value of $$\left(\frac{M_c}{M_r}\right)^{1/2} \cdot (2.21 \text{ Å})$$

corresponds to the (theoretical) freely rotating root mean square end-to-end distance of the gelatin chain between two crosslinks. Multiplication of this value with 2α' gives the experimental root mean square end-to-end distance between two crosslinks. The factor α' was assumed to have a value of 2, as reported for non-recombinant gelatins (4,5). $Q_m$ is the equilibrium volume swelling ratio. It is inverse to the polymer volume fraction at equilibrium swelling (υ2,s).

E. Release Experiments

Hydrogel cylinders loaded with protein were placed in glass vials containing 3 ml phosphate buffer of pH 7.4 with 0.05% $NaN_3$. The vials were stored in a shaking water bath at 37° C. At different time-points, 1 ml of the phosphate buffer was sampled, filled in low-binding Eppendorf tubes, and stored at -20° C. until analysis. The removed volume was replaced by fresh phosphate buffer solution. Samples were analyzed by HPLC using an Alltima C18 RP-HPLC column (Alltech, Deerfield, Ill.). The injection volume was 40 microliter. A linear gradient was run that changed the starting mixture of 70% eluent A (10% acetonitrile, 90% water, 0.1% trifluoroacetic acid) and 30% eluent B (90% acetonitrile, 10% water, 0.1% trifluoroacetic acid) to 55% eluent A and 45% eluent B in 15 min. Return to the starting eluent composition occurred in one minute. Detection was by UV absorption at 280 nm, and protein concentration was determined by the area under the curve (AUC) of the HPLC signals using standards prepared from the protein stock solutions.

Results

In the tables below the released fraction of proteins Lysozyme and BSA from the hydrogels prepared at various concentrations is shown after 24 hours. At this time scale the sample was in so-called equilibrium and there was no additional protein released by diffusion. Hence the remaining non-released protein fraction is trapped inside the hydrogel and should be released by enzymatic degradation. It is this enzymatic degradation time scale of weeks or months which is of great importance for drug delivery devices

TABLE II

Diffusional release of Lysozyme and BSA from HU-4 hydrogels

| [HU4] v/v % | DS | ξ (nm) | $R_{H'}$ Lysozyme (nm) | ξ/$R_H$ | Released fraction | $R_{H'}$ BSA (nm) | ξ/$R_H$ | Released fraction |
|---|---|---|---|---|---|---|---|---|
| 10 | 1 | 86 | 2 | 21 | 0.98 | 6 | 7 | 0.96 |
| 20 | 1 | 26 | 2 | 6.5 | 0.86 | 6 | 2.2 | 0.80 |
| 30 | 1 | 6 | 2 | 3 | 0.83 | 6 | 1 | 0.13 |
| 40 | 1 | 3 | 2 | 1.5 | 0.48 | 6 | 0.5 | 0.12 |

TABLE III

Diffusional release of Lysozyme and BSA from CBE hydrogels

| [CBE] v/v % | DS | $\xi$ (nm) | $R_H$, Lysozyme (nm) | $\xi/R_H$ | Re- leased fraction | $R_H$, BSA (nm) | $\xi/R_H$ | Re- leased fraction |
|---|---|---|---|---|---|---|---|---|
| 10 | 1 | 45 | 2 | 22.5 | 0.99 | 6 | 7.5 | 0.97 |
| 20 | 1 | 8 | 2 | 4 | 0.95 | 6 | 1.3 | 0.4 |
| 30 | 1 | 5 | 2 | 2.5 | 0.83 | 6 | 0.9 | 0.16 |
| 40 | 1 | 2 | 2 | 1 | 0.3 | 6 | 0.3 | 0.10 |

TABLE IV

Diffusional release of Lysozyme and BSA from CBE5 hydrogels

| [CBE5] v/v % | DS | $\xi$ (nm) | $R_H$, Lysozyme (nm) | $\xi/R_H$ | Re- leased fraction | $R_H$, BSA (nm) | $\xi/R_H$ | Re- leased fraction |
|---|---|---|---|---|---|---|---|---|
| 10 | 1 | 28 | 2 | 14 | 0.99 | 6 | 4.7 | 0.97 |
| 20 | 1 | 10 | 2 | 5 | 0.95 | 6 | 1.7 | 0.2 |
| 30 | 1 | 4 | 2 | 2 | 0.7 | 6 | 0.7 | 0.11 |
| 40 | 1 | 1.2 | 2 | 0.6 | 0.2 | 6 | 0.2 | 0.05 |

TABLE V

Diffusional release of Lysozyme and BSA from P4-hydrogels

| [P4] v/v % | DS | $\xi$ (nm) | $R_H$, Lysozyme (nm) | $\xi/R_H$ | Re- leased fraction | $R_H$, BSA (nm) | $\xi/R_H$ | Re- leased fraction |
|---|---|---|---|---|---|---|---|---|
| 10 | 1 | 50 | 2 | 25 | 0.99 | 6 | 8.3 | 0.96 |
| 20 | 1 | 27 | 2 | 13.5 | 0.98 | 6 | 4.5 | 0.80 |
| 30 | 1 | 12 | 2 | 6 | 0.84 | 6 | 2 | 0.25 |
| 40 | 1 | 4 | 2 | 2 | 0.5 | 6 | 0.7 | 0.12 |

TABLE VI

Diffusional release of Lysozyme and BSA from hydrogels of acid treated hydrolysed porcine gelatin

| [porc. gelatin] v/v % | DS | $\xi$ (nm) | $R_H$, Lysozyme (nm) | $\xi/R_H$ | Re- leased fraction | $R_H$, BSA (nm) | $\xi/R_H$ | Re- leased fraction |
|---|---|---|---|---|---|---|---|---|
| 10 | 1 | 70 | 2 | 35 | 0.98 | 6 | 11.7 | 0.96 |
| 20 | 1 | 22 | 2 | 11 | 0.98 | 6 | 3.7 | 0.80 |
| 30 | 1 | 10 | 2 | 5 | 0.90 | 6 | 1.7 | 0.70 |
| 40 | 1 | 5 | 2 | 2.5 | 0.85 | 6 | 0.9 | 0.38 |

TABLE VII

Diffusional release of Lysozyme and BSA from hydrogels of hydrolysed alkali-treated bovine gelatin

| [bov. gelatin] v/v % | DS | $\xi$ (nm) | $R_H$, Lysozyme (nm) | $\xi/R_H$ | Re- leased fraction | $R_H$, BSA (nm) | $\xi/R_H$ | Re- leased fraction |
|---|---|---|---|---|---|---|---|---|
| 10 | 1 | 56 | 2 | 28 | 0.98 | 6 | 9.3 | 0.96 |
| 20 | 1 | 12 | 2 | 6 | 0.98 | 6 | 2 | 0.72 |
| 30 | 1 | 7 | 2 | 3.5 | 0.80 | 6 | 1.2 | 0.63 |
| 40 | 1 | 3 | 2 | 1.5 | 0.53 | 6 | 0.5 | 0.30 |

From the above results it becomes clear that in order to have a reasonable fraction of the protein trapped inside the hydrogel the hydrodynamic radius should be significantly large with respect to the mesh or pore size of the hydrogel network. This mesh size is governed by the concentration of the gelatin used and the degree of substitution, which together determine the crosslink density.

In other words, it is clearly seen that if the ratio $\xi/R_H$ is larger than 2 a significant part of the therapeutic protein is being released by diffusion, causing an undesirable initial burst of therapeutic protein.

Another surprising effect of the above invention is that recombinant gelatins show less diffusional release at a given ratio $\xi/R_H$ compared to conventional gelatins. Although more research is required to explain this effect it is speculated that the homogeneous and mono-disperse nature of the recombinant gelatins is contributing to the improved behaviour in contrast to the heterogeneous and poly-disperse nature of natural gelatins causing local inhomogeneities in the hydrogels on a microscopic level. These inhomogeneities may be related to the presence of small fragments of less than e.g. 2.5 kDa. In a less dense region one may envisage that diffusional release might still occur.

Furthermore it also becomes clear that CBE and CBE5 gelatin with their enhanced lysine amount compared to the other gelatins exhibit a decreased mesh size. Apparently this is due to the increased number of cross-links by the increased lysine amount. Hence these specific gelatins may be preferentially used for controlled release applications.

DESCRIPTION OF FIGURES

FIG. 1

Amino acid sequence of HU4 gelatin.

FIG. 2

Amino acid sequence of CBE.

FIG. 3

Amino acid sequence of CBE5.

FIG. 4

Amino acid sequence of P4.

REFERENCES

1. T. K. L. Meyvis, B. G. Stubbe, M. J. van Steenbergen, W. E Hennink, S. C. De Smedt and J. Demeester. A comparison between the use of dynamic mechanical analysis and oscillatory shear rheometry for the characterisation of hydrogels. Int J Pharm 244: 163-168 (2002).
2. W. W. Graessly. Viscoelasticity and flow in polymeric liquids. In J. E. Mark, K. L. Ngai, W. W. Graessly, L. Mandelkern, E. T. Samulski, J. L. Koenig and G. D. Wignall (eds), Physical properties of polymers. Cambridge University Press, Cambridge, 2004.
3. R. J. Stenekes, S. C. De Smedt, J. Demeester, G. Sun, Z. Zhang and W. E. Hennink. Pore sizes in hydrated dextran microspheres. Biomacromolecules 1: 696-703 (2000).
4. J. W. Mwangi and C. M. Ofner. Crosslinked gelatin matrices: release of a random coil macromolecular solute. Int J Pharm 278: 319-327 (2004).
5. A. Veis. The macromolecular chemistry of gelatin, Academic Press, New York, 1964.

The invention claimed is:

1. A controlled release composition comprising a cross-linked recombinant non-hydroxylated gelatin and at least one therapeutic protein wherein the ratio of the average mesh size ($\xi$) of the gelatin matrix and the average hydrodynamic radius ($R_H$) of said therapeutic protein is smaller than 2, wherein the cross-linked recombinant non-hydroxylated gelatin is free of low molecular weight peptides below 2.5 kiloDaltons.

2. A controlled release composition according to claim 1 wherein the gelatin is non-glycosylated.

3. A controlled release composition according to claim 1, wherein release rate of the therapeutic protein from said controlled release composition is such that less than 50%, of the fraction of the therapeutic protein entrapped in the controlled release composition is released in a period of 24 hours when the controlled release composition is placed in aqueous solution.

4. A controlled release composition according to claim 1, wherein said gelatin is human or human-like recombinant gelatin.

5. A controlled release composition according to claim 2, wherein said gelatin is human or human-like recombinant gelatin.

6. A controlled release composition according to claim 3, wherein said gelatin is human or human-like recombinant gelatin.

7. A controlled release composition according to claim 1, wherein said gelatin is chemically modified with a cross-linkable group selected from the group consisting of acrylates and methacrylates.

8. A controlled release composition according to claim 2, wherein said gelatin is chemically modified with a cross-linkable group selected from the group consisting of acrylates and methacrylates.

9. A controlled release composition according to claim 3, wherein said gelatin is chemically modified with a cross-linkable group selected from the group consisting of acrylates and methacrylates.

10. A controlled release composition according to claim 4, wherein said gelatin is chemically modified with a cross-linkable group selected from the group consisting of acrylates and methacrylates.

11. A controlled release composition according to claim 1, wherein said cross-linked gelatin is obtained by redox polymerisation or radical polymerisation initiated by an initiator selected from the group of a type I photo-initiator, a type II photo-initiator, an organic peroxide such as benzoyl peroxide, and mixtures such as a mixture of potassium peroxodisulfate and N,N,N',N' tetramethylethyenediamine.

12. A controlled release composition according to claim 2, wherein said cross-linked gelatin is obtained by redox polymerisation or radical polymerisation initiated by an initiator selected from the group of a type I photo-initiator, a type II photo-initiator, an organic peroxide such as benzoyl peroxide, and mixtures such as a mixture of potassium peroxodisulfate and N,N,N',N' tetramethylethyenediamine.

13. A controlled release composition according to claim 3, wherein said cross-linked gelatin is obtained by redox polymerisation or radical polymerisation initiated by an initiator selected from the group of a type I photo-initiator, a type II photo-initiator, an organic peroxide such as benzoyl peroxide, and mixtures such as a mixture of potassium peroxodisulfate and N,N,N',N' tetramethylethyenediamine.

14. A controlled release composition according to claim 4, wherein said cross-linked gelatin is obtained by redox polymerisation or radical polymerisation initiated by an initiator selected from the group of a type I photo-initiator, a type II photo-initiator, an organic peroxide such as benzoyl peroxide, and mixtures such as a mixture of potassium peroxodisulfate and N,N,N',N' tetramethylethyenediamine.

15. A pharmaceutical composition comprising a controlled release composition according to claim 1.

16. A pharmaceutical composition comprising a controlled release composition according to claim 8.

17. A pharmaceutical comprising a controlled release composition according to claim 1.

18. A pharmaceutical comprising a controlled release composition according to claim 8.

19. A controlled release composition according to claim 1 comprising a compound or drug for treatment of pain, cancer therapy, cardiovascular diseases, myocardial repair, angiogenesis, bone repair and regeneration, wound treatment, neural stimulation/therapy or diabetics.

20. A controlled release composition according to claim 10 comprising a compound or drug for treatment of pain, cancer therapy, cardiovascular diseases, myocardial repair, angiogenesis, bone repair and regeneration, wound treatment, neural stimulation/therapy or diabetics.

* * * * *